US006416808B1

(12) United States Patent
Crea (10) Patent No.: US 6,416,808 B1
(45) Date of Patent: Jul. 9, 2002

(54) METHOD OF OBTAINING A HYDROXYTYROSOL-RICH COMPOSITION FROM VEGETATION WATER

(75) Inventor: Roberto Crea, San Mateo, CA (US)

(73) Assignee: CreAgri, Inc., Hayward, CA (US)

( * ) Notice: Subject to any disclaimer, the term of this patent is extended or adjusted under 35 U.S.C. 154(b) by 0 days.

(21) Appl. No.: 09/944,744

(22) Filed: Aug. 31, 2001

Related U.S. Application Data (60) Provisional application No. 60/230,535, filed on Sep. 1, 2000.

(51) Int. Cl.$^7$ ................ A23D 7/00; A61K 31/7048; A61K 31/05
(52) U.S. Cl. ............... 426/601; 514/27; 514/738
(58) Field of Search .................. 514/738, 27; 426/601

(56) References Cited

U.S. PATENT DOCUMENTS

| | | | |
|---|---|---|---|
| 4,370,274 A | 1/1983 | Finch et al. | 260/412.3 |
| 4,452,744 A | 6/1984 | Finch et al. | 260/412.2 |
| 4,522,119 A | 6/1985 | Finch et al. | 99/483 |
| 5,714,150 A | 2/1998 | Nachman | 424/195.1 |
| 6,197,308 B1 | 3/2001 | Crea et al. | 424/195.1 |

FOREIGN PATENT DOCUMENTS

| | | |
|---|---|---|
| EP | 581748 A1 | 2/1994 |
| ES | 2006904 | 5/1989 |
| WO | WO 97/28089 | 8/1997 |
| WO | 97/47711 | * 12/1997 |
| WO | 00/36936 | * 6/2000 |

OTHER PUBLICATIONS

Saija et al., International Journal of Pharmaceutics, 166, 123–133 (1998).*

Aziz, N.H., et al., "Comparative antibacterial and antifungal effects of some phenolic compounds" *Microbios* 93:43–54 (1998).

Computer Abstract FSTA 97 (01):J0083 Limiroli et al. "1H NMR Study of Phenolics in the Vegetation Water of Three Cultivars of Olea Europaea" Journal of Agric. & Food Chem. (1996) 44 (8) 2040–2048.

Computer Abstract FSTA 2000 (01):N0049 Servill et al. "High Performance Liquid Chromatography Evaluation of Phenols in Olive Fruit, Virgin Oil, Vegetation Waters, and Pomace and 1D–and 2D–Nuclear Magnetic Resonance Characterization", Jourof the Amer. Oil Chemists Soc. (1999) 76 (7).

Computer Abstract Energy 1992 (16) :116698 Amalfitano "Recovery and Purification Treatments of Water Coming form Olive Oil Extraction Processes", "Energy Innovation and the Agro–Food Industry" Ed. Corte et al. Conference: Mar. 21–23, 1990.

de la Puerta, et al., "Inhibition of Leukocyte 5–Lipoxygenase by Phenolics from Virgin Olive Oil" *Biochemical Pharmacology* 57:445–449 (1999).

Koutsoumanis, K., et al., "Modelling the effectiveness of a natural antimicrobial on Salmonella enteritidis as a function of concentration, temperature and pH, using conductance measurements" *J. of Applied Microbiology* 84:981–987 (1998).

Tassou, C.C. and Nychas, G.J.E., "Inhibition of Salmonella enteritidis by oleuropein in broth and in a model food system" *Letters in Applied Microbiology* 20:120–124 (1995).

Tranter, H.S., et al., "The effect of the olive phenolic compound, oleuropein, on growth and enterotoxin B production by *Staphylococcus aureus*" *J. of Applied Bacteriology* 74:253–259 (1993).

Visioli, F., et al., "Free Radical–Scavenging Properties of Olive Oil Polyphenols" *Biochemical and Biophysical Communications* 247:60–64 (1998).

Visioli, F., et al., "Oleuropein, the Bitter Principle of Olives, Enhances Nitric Oxide Production by Mouse Macrophages" *Life Sciences* 62 (6):541–546 (1998).

Visioli, F., et al., "'Waste Waters' from Olive Oil Production are Rich in Natural Antioxidants" *Experientia, Birkhauser Verlag* 51(1):32–34 (1995).

* cited by examiner

Primary Examiner—Phyllis G. Spivack
(74) Attorney, Agent, or Firm—Perkins Coie LLP; Peter J. Dehlinger; Larry W. Thrower (57) ABSTRACT

The invention provides an olive-derived dietary supplement comprising hydroxytyrosol and oleoeuropein in specific weight ratios.

6 Claims, 5 Drawing Sheets

METHOD OF OBTAINING A HYDROXYTYROSOL-RICH COMPOSITION FROM VEGETATION WATER

This application claims the benefit of U.S. Provisional Application No. 60/230,535 filed Sep. 1, 2000, which is expressly incorporated herein by reference in its entirety.

FIELD OF THE INVENTION

This invention relates to a phenolic fraction of a group of compounds present in olive plants known as hydroxytyrosol (3,4-dihydroxyphenylethanol). Particularly, the invention provides an olive extract containing hydroxytyrosol, with low amounts or substantially free of oleoeuropein and tyrosol, and a method of obtaining the same.

REFERENCES

Armstrong, B. K. and Doll, R., *International. J. Cancer* 15:617–631 (1975).

Bartsch, H., et al., *Carcinogenesis* 20:2209–2218 (1999).

Braga, C., et al., *Cancer* 82:448–453 (1998).

Chan, J. M., et al., *Seminars in Cancer Biology* 8:263–273 (1998).

d'Amicis, A. and Farchi, S., in: Advances in Nutrition and Cancer 2 (Zappia, V., et al., Eds.) 67–72, Kluwer Academic/Plenum Publishers, New York (1999).

Deiana, M., et al., *Free Radic. Biol. Med.* 26:762–769 (1999).

de la Puerta, R., et al., *Biochem. Pharmacol.* 57:445–449 (1999).

Ficarra, P., et al, *Farmaco* 46:803–815 (1991).

Gerber, M., *Epidemiology of Diet and Cancer*, ed. M. J. Hill, 263–275 (1994).

Kohyama, N., et al., *Biosci. Biotechnol. Biochem.* 61:347–350 (1997).

Kuller, L. H., *Journal of the American Dietetic Association* 97:S9–S15 (1997).

La Vecchia, C., et al., *European Journal of Cancer Prevention* 7:461–464 (1998).

Manna, C., et al., *FEBS Letters* 470:341–344 (2000).

Martin-Moreno, J. M., et al., *Int. J. Cancer* 58:774–780 (1994).

Mattson, F. H. and Grundy, S. M., *J. Lipid Res.* 26:194–202 (1985).

Owen, R. W., et al., *J. Can. Res. Clin. Onc.* 125:S31 (2000a).

Owen, R. W., et al., *Eur. J. Cancer* 36:1235–1247 (2000b).

Owen, R. W., et al., *Food Chem. Toxic.* 38:647–659 (2000c).

Parthasarathy, S., et al., *Proc. Natl. Acad. Sci. USA* 87:3894–3898 (1990).

Petroni, A., et al., *Thromb. Res.* 78:151–160 (1995).

Risch, H. A., et al., *Journal of the National Cancer Institute* 86:1409–1415 (1994).

Romani, A., et al., *J. Agric. Food Chem.* 47:964–967 (1999).

Tsimidou, M., et al., *Food Chem.* 44:53–60 (1992).

Visioli, F., et al., *FEBS Letters* 468:159–160 (2000).

Visioli, F. and Galli, C., *Nutr. Rev.* 56:142–147 (1998).

BACKGROUND OF THE INVENTION

A high amount of dietary fat has been implicated in the development of several diseases (Owen et al., 2000c). Atherosclerosis (Kuller, 1997) and coronary heart disease (Gerber, 1994), as well as cancer of the breast (La Vecchia et al., 1998), prostate (Chan et al., 1998), ovary (Risch et al., 1994), and colon (Armstrong and Doll, 1975) have each been associated with elevated dietary fat. However, evidence indicates that it is not only the amount, but also the type of dietary fat that is important in the etiology of some cancers (Bartsch et al., 1999).

Olive oil, the principal fat component of the Mediterranean diet, has been associated with a lower incidence of coronary heart disease (Owen et al., 2000b; Parthasarathy et al., 1990; Mattson and Grundy, 1985) and certain cancers (d'Amicis and Farchi, 1999; Braga et al., 1998; Martin-Moreno et al., 1994). Several laboratories have reported that the hydrolysis of the olive oil phenolics oleuropin and other family members lead to small phenolic components with strong chemoprotective activity (Owen et al., 2000a; Manna et al., 2000). In particular, the olive oil phenolic hydroxytyrosol prevents low density lipoprotein (LDL) oxidation (Visioli and Galli, 1998), platelet aggregation (Petroni et al., 1995), and inhibits 5- and 12-lipoxygenases (de la Puerta et al., 1999; Kohyama et al., 1997). Hydroxytyrosol has also been found to exert an inhibitory effect on peroxynitrite dependent DNA base modification and tyrosine nitration (Deiana et al., 1999), and it counteracts cytotoxicity induced by reactive oxygen species in various human cellular systems (Manna et al., 2000). Finally, studies have shown that hydroxytyrosol is dose-dependently absorbed in humans following ingestion, indicating its bioavailability (Visioli et al, 2000).

Conventionally, olive oil production involves crushing olives, including the pits, to produce a thick paste. During this procedure, the crushed olives are continuously washed with water, a process known as "malaxation." The paste is then mechanically pressed to squeeze out the oil content. In addition to providing olive oil, the pressing also squeezes out the paste's water content. Such washing and pressing steps yield a considerable amount of water, referred to as "vegetation water."

Both the pit and the pulp of olives are rich in water-soluble, phenolic compounds. Such compounds are extracted from olives during malaxation, according to their partition coefficients, and end up in the vegetation water. This explains why various phenolic compounds, such as oleoeuropein and its derivatives, produced in olive pulp, can be found in abundance in vegetation waters. Similarly, a number of monophenolic compounds, such as tyrosol and its derivatives, produced in olive pits, are also abundant in vegetation waters.

Because of the strong chemoprotective activity of hydroxytyrosol, it is desirable to develop a method which produces an aqueous olive extract with a high percentage of hydroxytyrosol.

SUMMARY OF THE INVENTION

In one aspect, the invention includes a method of producing a hydroxytyrosol-rich composition. The method has the steps of (a) producing vegetation water from olives, preferably depitted olive meat, (b) adding acid to the vegetation water in an amount effective to produce a pH between 1 and 5, preferably 2–4, and (c) incubating the acidified vegetation water for a period of at least two months, typically 6–12 months until at least 75%, and preferably at least 90% of the oleoeuropein originally present in the vegetation water has been converted to hydroxytyrosol.

In one embodiment, the incubating is carried out until the vegetation water has a weight ratio of hydroxytyrosol to oleoeuropein of between 5:1 and 200:1, preferably 10:1 and 100:1. In a related embodiment, the incubating is carried out until the vegetation water has a weight ratio of hydroxytyrosol and tyrosol of between 3:1 and 50:1, typically 5:1 to 30:1.

The method may further include fractionating the incubated, vegetation water to separate hydroxytyrosol from other components, and/or drying the vegetation water of isolated hydroxytyrosol to produce a dried extract.

In another aspect, the invention includes a method of producing a hydroxytyrosol-rich composition that includes the steps of (a) producing vegetation water from olives; (b) optionally, drying the vegetation water; (c) contacting the optionally dried vegetation water with a supercritical fluid; and (d) recovering the hydroxytyrosol-rich composition from the contacted vegetation water. In one embodiment, the hydroxytyrosol-rich composition includes at least about 95 percent by weight hydroxytyrosol. In another embodiment, the hydroxytyrosol-rich composition includes at least about 97 percent by weight hydroxytyrosol. In yet another embodiment, the hydroxytyrosol-rich composition includes at least about 99 percent by weight hydroxytyrosol.

In one embodiment, the recovering step described above includes the steps of (a) recovering the supercritical fluid, where the supercritical fluid contains the hydroxytyrosol; and (b) vaporizing the supercritical fluid to extract the hydroxytyrosol-rich composition. In another embodiment, the contacting step described above comprises the steps of (a) providing a porous membrane having opposite sides in a module under pressure with the membrane serving as a barrier interface between a fluid and a dense gas, the membrane being nonselective for said hydroxytyrosol; (b) providing the supercritical fluid into the module on one side of the membrane and the vegetation water on the opposite side of the membrane; (c) and extracting the hydroxytyrosol across the membrane as driven by a concentration gradient of the hydroxytyrosol between the vegetation water and the supercritical fluid. In one embodiment, the porous membrane is a hollow fiber membrane. In another embodiment, the supercritical fluid is carbon dioxide.

In another aspect, the invention includes a dietary supplement comprising an aqueous extract of olives containing a weight ratio of hydroxytyrosol to oleoeuropein of between 5:1 and 200:1, typically 10:1 and 100:1.

In a related aspect the invention includes a dietary supplement comprising an aqueous extract of olives containing a weight ratio of hydroxytyrosol and tyrosol of between 3:1 and 50:1, typically 5:1 and 30:1.

The above supplements may be dried to provide a powder extract, which can formulated into a tablet, capsule, pill, or confection food additive.

These and other objects and features of the invention will be more fully appreciated when the following detailed description of the invention is read in conjunction with the accompanying figure and tables.

DETAILED DESCRIPTION OF THE INVENTION

I. Definitions

Unless otherwise indicated, all terms used herein have the same meaning as they would to one skilled in the art of the present invention. It is to be understood that this invention is not limited to the particular methodology, protocols, and reagents described, as these may vary.

Figure 1:
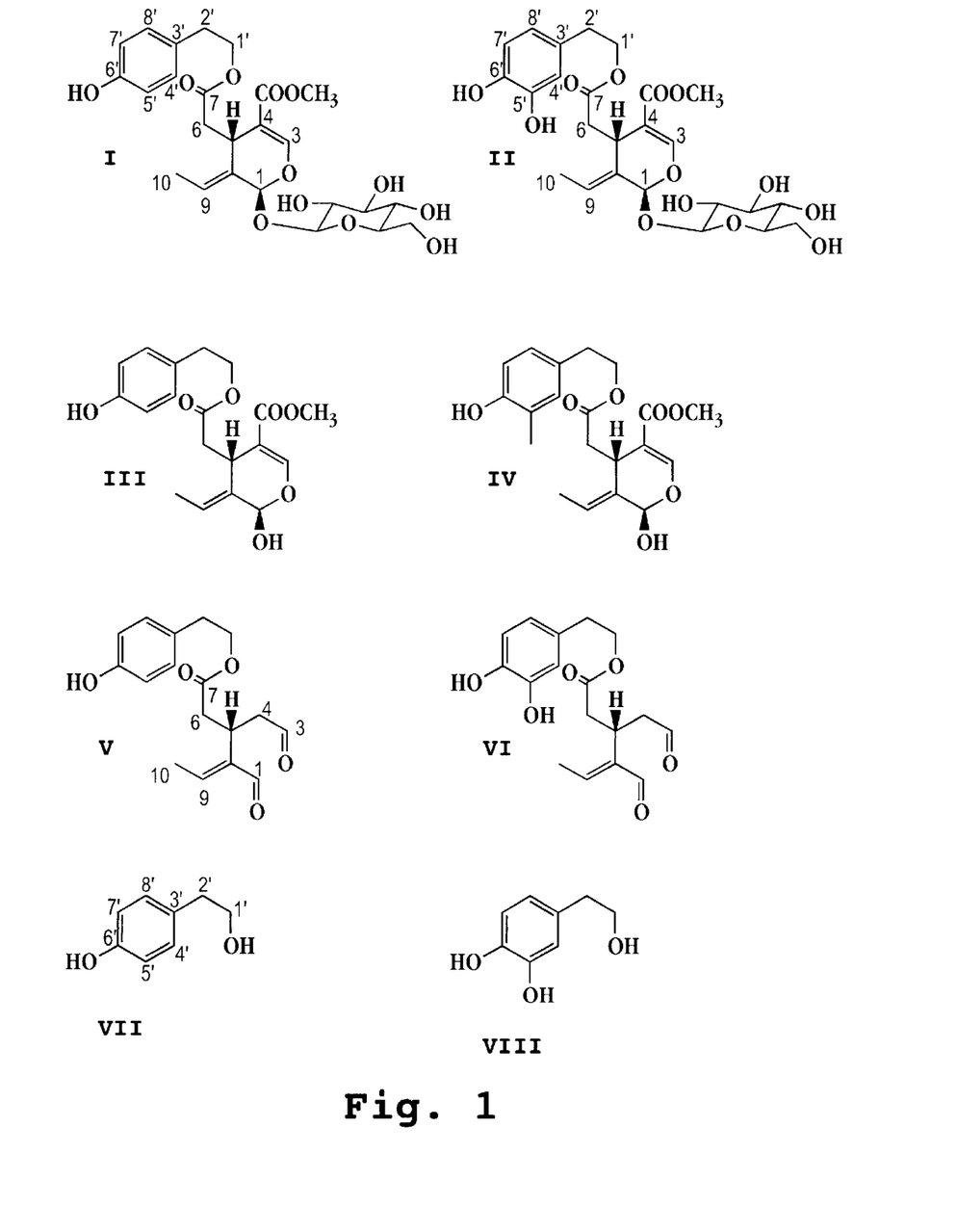
FIG. 1 shows the structures of phenolic compounds and their precursors detected in olive oil: ligstroside (I); oleuropein glucoside (II); aglycone of ligstroside (III); aglycone of oleuropein glucoside (IV); dialdehydic form of ligstroside aglycone lacking a carboxymethyl group (V); dialdehydic form of oleuropein glucoside aglycone lacking a carboxymethyl group (VI); tyrosol (VII); hydroxytyrosol (VIII).

By "oleoeuropein" is intended secoiridoid glucoside oleuropein (Structure II in FIG. 1).

By "tyrosol" is intended 4-hydroxyphenethyl alcohol (Structure VII in FIG. 1).

By "hydroxytyrosol" is intended 3,4-dihydroxyphenethyl alcohol (Structure VIII in the FIG. 1).

II. Method of the Invention

The invention provides, in one aspect, provides a hydroxytyrosol-rich composition from olive-derived vegetation water. It has been discovered that under specific conditions, as described below, hydroxytyrosol may be obtained from the vegetation water of olives. Considered below are the steps in practicing the invention.

A. Producing Vegetation Water

The method of the invention employs olives that may be obtained from conventional and commercially available sources such as growers. Preferably, the vegetation water is obtained from pitted olives. The olives processed according to the method disclosed herein may be pitted by any suitable means. Pits in the olives contain tyrosol which is an undesired component in the vegetation water and which may not be appreciably broken down by the acid treatment described below. The pits may be separated from the pulp manually or in an automated manner as described below. Preferably, such means should be capable of segregating the pits without breaking them, which might otherwise cause higher concentrations of tyrosol in the vegetation water. In another embodiment, hydroxytyrosol is extracted from vegetation water obtained from olives that have not been pitted.

To produce vegetation water, olive pulp from the olives is first pressed to obtain a liquid-phase mixture including olive oil, vegetation water, and solid by-products. Thereafter, the vegetation water is separated from the rest of the liquid phase mixture and collected. Exemplary methods of obtaining vegetation water are described in co-owned U.S. Pat. Nos. 6,165,475 and 6,197,308, both to R. Crea, each of which are expressly incorporated herein by reference in their entirety.

For purposes of commercial production, it may be desirable to automate various aspects of the invention. In this regard, one embodiment contemplates the use of an apparatus as disclosed in U.S. Pat. Nos. 4,452,744, 4,522,119 and 4,370,274, each to Finch et al., and each expressly incorporated herein by reference. Briefly, Finch et al. teach an apparatus for recovering olive oil from olives. Initially, olives are fed to a pulper that separates the olive pits from the olives to obtain a pitless olive meat. The meat is then taken up by an extraction screw that subjects the meat to an extraction pressure sufficient to withdraw a liquid phase, comprising oil, water and a minor proportion of olive pulp. The liquid phase is collected in a bin and then sent to a clarifying centrifuge that separates the pulp from the liquid phase to obtain a mixture comprising olive oil and vegetation water. A purifying centrifuge then separates the vegetation water and a small proportion of solid matter from the mixture to obtain an olive oil, substantially free of vegetation water, that is collected in a tank. According to Finch et al., the water is put to a disposal means such as a sewer. The present invention, in sharp contrast, provides for the collection, saving and use of the vegetation water to extract hydroxytyrosol.

Additional devices that may be used in practicing the present invention are disclosed in Italian Pat. Nos. 1276576 and 1278025, each of which is expressly incorporated herein by reference. As above, these devices can be used to separate the pulp from the pits prior to processing of the crushed olive pulp into oil, water, and solid residues.

B. Conversion of Oleoeuropein to Hydroxytyrosol

In one aspect of the invention, the oleoeuropein contained in the vegetation water is converted to hydroxytyrosol. The pH of the vegetation water may be decreased by the addition of acid, and the vegetation water allowed to incubate under conditions which, according to the discovery of the invention, promote acid hydrolysis of oleoeuropein to hydroxytyrosol. The sample may then be fractionated to separate hydroxytyrosol from other compounds.

In a preferred embodiment, the added acid is citric acid. The acid is added to the vegetation water to adjust the pH to 1–5, preferably 2–4. Solid citric acid can be added while continuously stirring in an amount of preferably about 25 to 50 pounds of acid per about 1000 gallons of vegetation water. The pH of the resulting solution can be monitored, and further addition of acid may be necessary to achieve the desired pH. Exemplary methods showing the conversion of oleoeuropein to hydroxytyrosol following the addition of citric acid are given in Examples 1 and 2.

The acid may also be an organic or inorganic acid other than citric acid. Exemplary acids which may be used in the present invention include the inorganic substances known as the mineral acids—sulfuric, nitric, hydrochloric, and phosphoric acids—and the organic compounds belonging to the carboxylic acid, sulfonic acid, and phenol groups. The addition of acid to the vegetation water serves several purposes: (i) it stabilizes the vegetation water; (ii) it prevents fermentation of the vegetation water; and (iii) it slowly hydrolizes the oleouropein, converting it to hydroxytyrosol, as shown in Examples 1 and 2. Tables 1 and 2, in Examples 1 and 2, respectively, contain data from two samples of vegetation water and the respective percent composition of various components in the samples over time following the addition of citric acid. In one embodiment, the mixture is allowed to incubate until hydroxytyrosol is 75–90% of the total combination of tyrosol and hydroxytyrosol, and substantially none of the oleoeuropein in the original mixture remains.

C. Purification of Hydroxytyrosol

Following the conversion of oleouropein to hydroxytyrosol, the incubated vegetation water may be fractionated by a number of methods known in the art. Alternatively, vegetation water may be fractionated prior to treatment with acid. Exemplary methods of fractionating include partitioning with an organic solvent, high pressure liquid chromatography (HPLC), or supercritical fluids.

Vegetation water obtained as described above provides a solution which is rich in low molecular weight polyphenols, particularly hydroxytyrosol and a small amount of tyrosol. The concentration of hydroxytyrosol in the processed water may range from 4–5 grams per liter to 10–15 grams per liter depending upon the degree of dilution during the olive oil extraction. In one embodiment, the invention provides a method of extraction or purification that selectively enriches the content of hydroxytyrosol without the addition of contaminants. Thus, the major polyphenolic component, hydroxytyrosol, is isolated from other members of the polyphenolic family, impurities, suspended solids, tannins, and other molecules contained in the vegetation water. Hydroxytyrosol may therefore be produced in a purity and quantity not readily available by current synthetic or natural extraction methods.

A supercritical fluid is a gas that becomes very dense above its critical temperature and pressure. Its properties are between those of a gas and liquid, resulting in increased ability to dissolve compounds. Its relatively high density, high diffusivity, and low viscosity allow it to extract compounds faster than conventional liquid solvents. Carbon dioxide is the gas used most widely for supercritical fluid processing of foods and food ingredients because it is natural, nontoxic, non-flammable, and relatively inert and leaves no residue in the extracted product. Typical liquid extraction with supercritical carbon dioxide is usually done by dispersing one phase in the other in large contacting columns or towers, where the solute containing fluid, such as juices, flows downward by gravity, and the supercritical carbon dioxide flows upward. Mass transfer occurs at the interface between the two phases.

Alternatively, continuous extraction of liquids and suspensions can be achieved using supercritical fluids, such as carbon dioxide, and porous membranes instead of contacting columns. Instead of dispersing the phases, the liquid is fed continuously through porous polypropylene membranes configured as hollow fiber bundles or spiral wound sheets. The liquid passes through the porous membranes within a pressurized module, while supercritical carbon dioxide flows countercurrently on the other side of the membrane. The pressure in the module is essentially the same, so that the extraction is driven by the concentration gradient between the fluid and the supercritical carbon dioxide. The extract may be recovered by vaporizing the carbon dioxide for recycling. An exemplary method of extraction using supercritical carbon dioxide and porous membranes is described in U.S. Pat. No 5,490,884, which is expressly incorporated by reference herein in its entirety.

Other supercritical fluids, instead of, or in combination with, carbon dioxide. These fluids include methane, ethane, propane, butane, isobutane, ethene, propene, hydrofluorocarbons, tetrafluoromethane, chlorodifluoromethane, carbon dioxide, dinitrogen monoxide, sulphur hexafluoride, ammonia, and methyl chloride.

Example 3 describes a small scale experiment in support of the invention, wherein hydroxytyrosol was isolated from vegetation water using supercritical carbon dioxide and porous membranes. HPLC and mass spectrometry analysis of the isolated hydroxytyrosol shows the sample to be 97–99% pure hydroxytyrosol. Thus, the invention provides a hydroxytyrosol-rich composition containing at least about 80% hydroxytyrosol, preferably at least about 90% hydroxytyrosol, more preferably at least about 95% hydroxytyrosol, even more preferably at least about 97% hydroxytyrosol, and yet, even more preferably at least about 99% hydroxytyrosol.

Prior to extraction with a supercritical fluid the vegetation water may have carriers, which are known to those of skill in the art, such as maltodextran and/or polypropylene beads, added to the solution; and/or the solution may be dried. The drying step preferably removes at least about 90%, more preferably at least about 95%, and even more preferably at least about 98% of the water from the vegetation water.

An important feature of membrane reactors is the fact that contact surface interfacial area can be added independently of fluid velocities. Accordingly, the invention contemplates a large scale unit where the surface membrane area of the membrane used for extraction is at least about 100 square yards, preferably at least about 300 square yards, and even more preferably at least about 600 square yards to allow separation of hydroxytyrosol from large volumes of vegetation water. Thus, the membrane system of the invention would, in one aspect, be able to accommodate a flow rate of between 1–20 liters per minute, preferably between 5–10 liters per minute.

Additional purification methods may also be used in accordance with the invention as mentioned above. HPLC isolation of hydroxytyrosine is described in: Ficarra et al., 1991; Romani et al., 1999; and Tsimidou, 1992, each of which is expressly incorporated by reference herein.

III. Hydroxytyrosol-Rich Dietary Supplement

It should be appreciated that hydroxytyrosol produced by the method described above may be used for a variety of applications. For example, hydroxytyrosol obtained by the method of the present invention can be used: (i) as a natural anti-bacterial, anti-viral and/or fungicidal product for agricultural and/or pest control applications, and (ii) as a therapeutic and/or an anti-oxidant for a variety of health purposes. In one exemplary embodiment, the hydroxytyrosol, is administered to a mammalian subject, such as a person desirous of one or more of the benefits associated with hydroxytyrosol.

The hydroxytyrosol obtained by the method of the invention can be administered orally or parenterally. Oral dosage forms can be in a solid or liquid form. Such dosage forms can be formulated from purified hydroxytyrosol or they can be formulated from aqueous or aqueous-alcoholic extracts. Regarding the latter, aqueous or aqueous-alcoholic (e.g., water-methanol or water-ethanol) extracts can be spray-dried to provide a dry powder that can be formulated into oral dosage forms with other pharmaceutically acceptable carriers. The aqueous or aqueous-alcoholic extracts can be formulated to contain various weight ratios of hydroxytyrosol to oleoeuropein of between 5:1 and 200:1, preferably between about 10:1 and about 100:1. The extracts may also be formulated to contain various weight ratios of hydroxytysol and tyrosol of between about 3:1 and about 50:1, preferably between about 5:1 and about 30:1.

The solid oral dosage form compositions in accordance with this invention are prepared in a manner well known in the pharmaceutical arts, and comprise hydroxytyrosol in combination with at least one pharmaceutically acceptable carrier. In making such compositions, a hydroxytyrosol-rich composition, either in substantially pure form or as a component of a raw distillate or extract, is usually mixed, diluted or enclosed with a carrier. The carrier can be in a solid form, semi-solid or liquid material which acts as a vehicle, carrier or medium for the active ingredient. Alternatively, the carrier can be in the form of a capsule or other container to facilitate oral administration. Thus, the solid oral dosage forms for administration in accordance with the present invention can be in the form of tablets, pills, powders or soft or hard gelatin capsules.

Alternatively, the hydroxytyrosol obtained in accordance with this invention for oral administration can be in liquid form wherein the pharmaceutically acceptable carrier is water or an aqueous-alcoholic medium.

The compositions for administration in the present invention can also be formulated with other common pharmaceutically acceptable excipients, including lactose, dextrose, sucrose, sorbitol, mannitol, starches, gums, calcium silicate, microcrystalline cellulose, polyvinylpyrrolidone, methylcellulose, water, alcohol and the like. The formulations can additionally include lubricating agents such as talc, magnesium stearate and mineral oil, wetting agents, emulsifying and suspending agents, preserving agents such as methyl- and propylhydroxybenzoates, sweetening agents or flavoring agents. Further, the compositions of the present invention can be formulated so as to provide quick, sustained or delayed release of the active ingredient after administration to a subject.

Parenteral formulations for use in accordance with the present invention are prepared using standard techniques in the art. They are commonly prepared as sterile injectable solutions, using a parenterally acceptable carrier such as isotonic saline solution or as a sterile packaged powder prepared for reconstitution with sterile buffer or isotonic saline prior to administration to a subject.

From the foregoing, it can be seen how various objects and features of the invention are met. Those skilled in the art can now appreciate from the foregoing description that the broad teachings of the present invention can be implemented in a variety of forms. Therefore, while this invention has been described in connection with particular embodiments and examples thereof, the true scope of the invention should not be so limited. Various changes and modification may be made without departing from the scope of the invention, as defined by the appended claims.

The following examples illustrate methods of producing hydroxytyrosol-rich compositions in accordance with the invention. The examples are intended to illustrate, but in no way limit, the scope f the invention.

EXAMPLES

Example 1

Conversion from Oleoeuropein to Hydroxytyrosol Following the Addition of About 25 Pounds of Citric Acid/1000 Gallons Table 1 shows the conversion of oleoeuropein to hydroxytyrosol over time following the addition of about 25 pounds of citric acid per 1000 gallons of vegetation water. The percentages in Table 1 are shown as weight percentages of the total phenolic compounds in the solution. As demonstrated in Table 1, hydroxytyrosol comprises over 80% of the phenolic compounds in the solution after 12 months.

TABLE 1

Conversion from Oleoeuropein to Hydroxytyrosol Following the Addition of About 25 Pounds of Citric Acid/1000 Gallons

| Component | Composition at T = 2 mo. | Composition at T = 3 mo. | Composition at T = 4.5 mo. | Composition at T = 12 mo. |
|---|---|---|---|---|
| Hydroxytyrosol | 30.4% | 32% | 48.4% | 80.2% |
| Tyrosol | 2.5% | 5% | 2.2% | 3.6% |
| Oleoeuropein | 41% | 36.6% | 25.1% | 1.2% |
| Oleoeuropein aglycone | 4.2% | 4.6% | 2.7% | 3.7% |

Example 2

Conversion from Oleoeuropein to Hydroxytyrosol Following the Addition of About 50 Pounds of Acid/1000 Gallons Table 2 shows the conversion of oleoeuropein to hydroxytyrosol over time following the addition of about 50 pounds of citric acid per 1000 gallons of vegetation water. The percentages in Table 2 are shown as weight percentages of the total phenolic compounds in the solution. Significantly, as demonstrated in Table 2, hydroxytyrosol comprises over 45% of the phenolic compounds in the solution after 2 months.

TABLE 2

Conversion from Oleoeuropein to Hydroxytyrosol Following the Addition of About 50 Pounds of Acid/1000 Gallons

| Component | Composition at T = 2 mo. | Composition at T = 12 mo. |
|---|---|---|
| Hydroxytyrosol | 45.7% | 78.5% |
| Tyrosol | 2.9% | 3.3% |
| Oleoeuropein | 28.7% | 1.5% |
| Oleoeuropein aglycone | 4.1% | 3.5% |

Example 3

Extraction of Hydroxytyrosol from Vegetation Water

Figure 2:
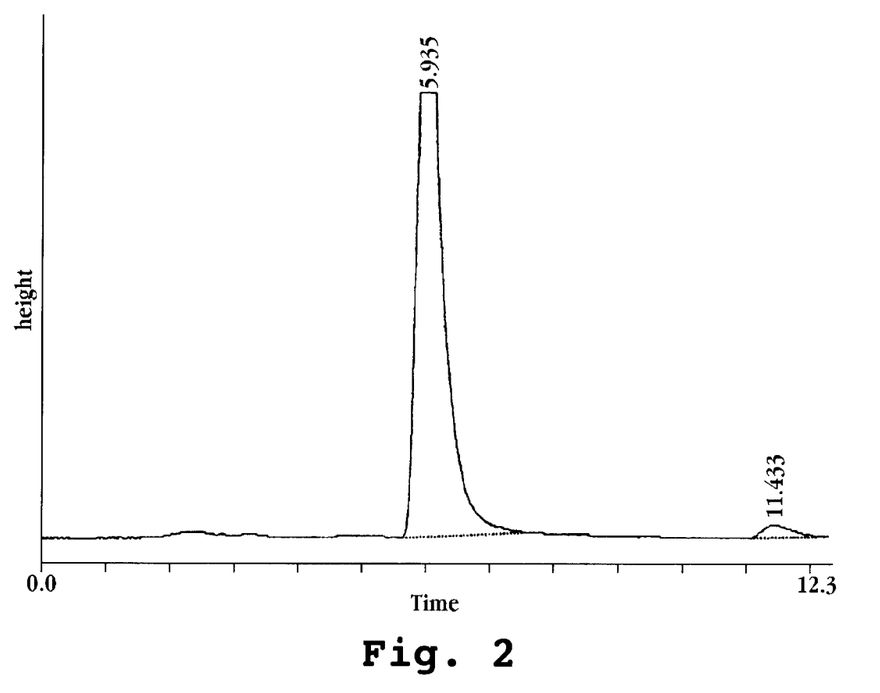
FIG. 2 shows the HPLC analysis of a hydroxytyrosol-rich composition of the invention after supercritical carbon dioxide extraction from vegetation water.
Figure 3:
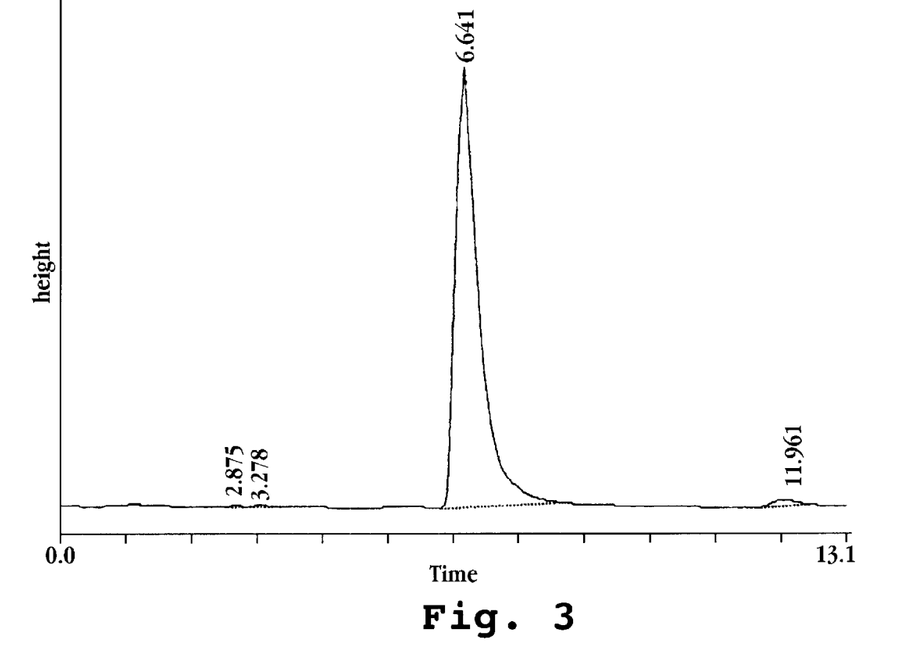
FIG. 3 shows the HPLC analysis of a hydroxytyrosol-rich composition of the invention following supercritical carbon dioxide extraction, with synthetic hydroxytyrosol.

An aliquot (0.5 ml) of vegetation water containing about 40 mg of dry solid (maltodextran) was mixed with polypropylene porous beads and dried. The dry mix was used for extraction with supercritical carbon dioxide (PoroCrit, LLC, Berkeley, Calif.). The collected sample (about 2.0 mg) was analyzed by HPLC. The profile of the sample is shown in FIG. 2, and Table 3 shows the area under the major peak to be 97%. When synthetic hydroxytyrosol was added to the sample and analyzed by HPLC, one major peak appeared, as shown in FIG. 3, indicating that the major product of the sample is hydroxytyrosol (Table 4).

Figure 4:
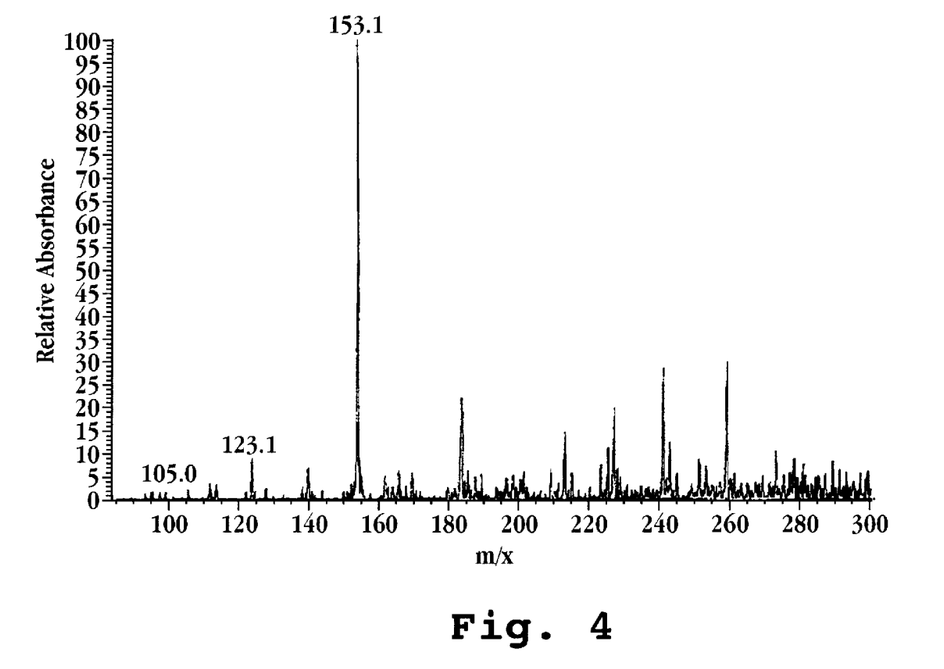
FIG. 4 shows the mass spectrum of a hydroxytyrosol-rich composition of the invention.
Figure 5:
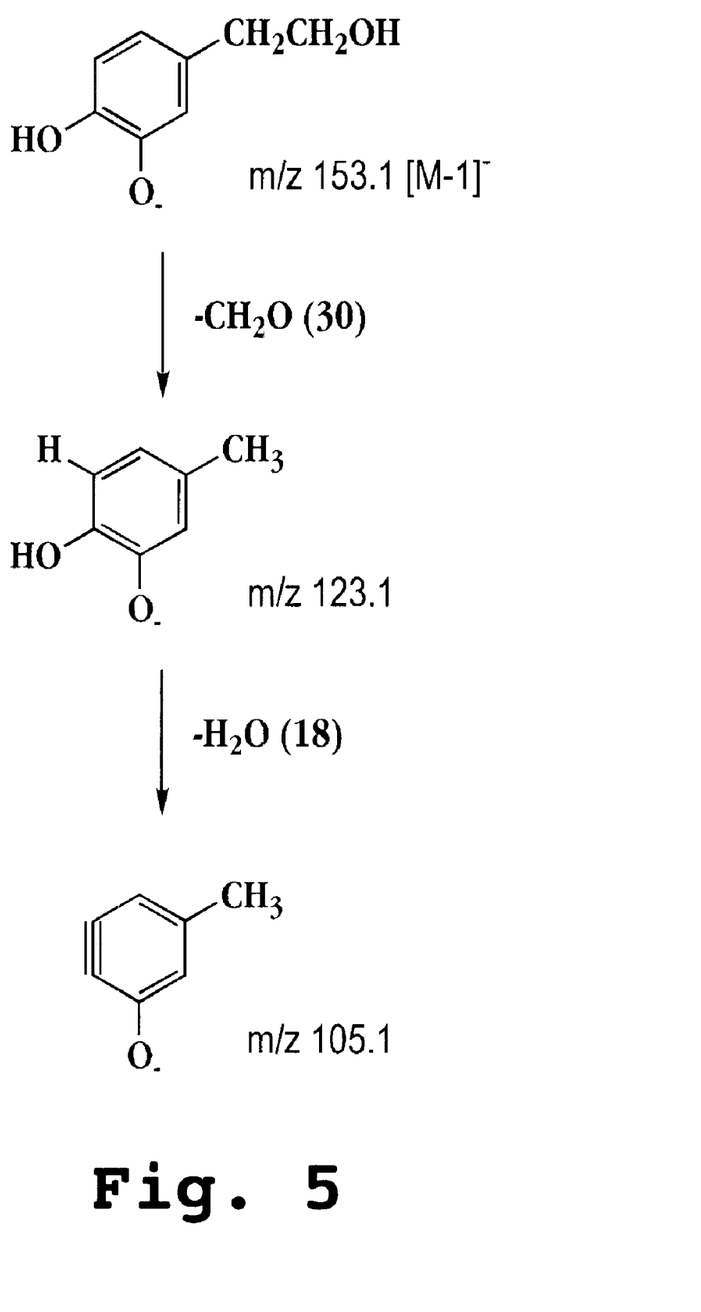
FIG. 5 illustrates the fragmentation pathway of hydroxytyrosol.

Mass spectrometry analysis of the sample, as shown in FIG. 4, confirmed that the major product is hydroxytyrosol. The sample was diluted to a final concentration of 26 micrograms per milliliter with methanol and analyzed in negative ionization mode on a Finnigan LCQ fitted with an ESI probe. The infusion was at 3 microliters per minute using an integrated syringe pump. The temperature was 270 C, needle voltage +4.2 V, sheath gas 45 units, and auxiliary gas 10 units. The fragmentation pathway of hydroxytyrosol is shown in FIG. 5. As can be seen in FIG. 4, hydroxytyrosol (mass/charge 153.1) and its fragmentation products (123.1 and 105.1 mass/charge) account for the majority of the product abundance in the multi-stage spectrum.

TABLE 3

Peak Analysis of FIG. 2 HPLC Results

| Peak No. | Time | Height ($\mu$V) | Area ($\mu$V-sec) | Area (%) |
|---|---|---|---|---|
| 1 | 5.935 | 215542 | 6687705 | 97.476 |
| 2 | 11.433 | 5686 | 173104 | 2.523 |

TABLE 4

Peak Analysis of FIG. 3 HPLC Results

| Peak No. | Time | Height ($\mu$V) | Area ($\mu$V-sec) | Area (%) |
|---|---|---|---|---|
| 1 | 2.875 | 1345 | 13895 | 0.26 |
| 2 | 3.278 | 1076 | 14140 | 0.265 |
| 3 | 6.641 | 211204 | 5241105 | 98.240 |
| 4 | 11.961 | 2587 | 65811 | 1.233 |

It is claimed:

1. A dietary supplement comprising an aqueous extract of olives containing a weight ratio of hydroxytyrosol to oleoeuropein of between about 5:1 and about 200:1.

2. The supplement of claim 1, which has a weight ratio of hydroxytyrosol to oleoeuropein of between about 10:1 and about 100:1.

3. The dietary supplement of claim 1, wherein said supplement is dried to provide a powder extract.

4. The dietary supplement of claim 1, wherein said extract is in the form of a tablet, capsule, pill, or confection food additive.

5. A dietary supplement comprising an aqueous extract of olives containing a weight ratio of hydroxytyrosol and tyrosol of between about 3:1 and about 50:1.

6. The dietary supplement of claim 5, containing a weight ratio of hydroxytyrosol and tyrosol of between about 5:1 and about 30:1.

* * * * *